(12) United States Patent
Johnson et al.

(10) Patent No.: US 8,257,408 B2
(45) Date of Patent: Sep. 4, 2012

(54) BONE PLATE AND BONE SCREW LOCKING SYSTEM

(75) Inventors: Jeffrey Johnson, Brandon, MS (US); Lawrence Walker, Madison, MS (US); Milton Phillips, Star, MS (US)

(73) Assignee: Spinal U.S.A., Pearl, MS (US)

( * ) Notice: Subject to any disclaimer, the term of this patent is extended or adjusted under 35 U.S.C. 154(b) by 149 days.

(21) Appl. No.: 12/635,116

(22) Filed: Dec. 10, 2009

(65) Prior Publication Data

US 2010/0234899 A1 Sep. 16, 2010

Related U.S. Application Data

(60) Provisional application No. 61/121,321, filed on Dec. 10, 2008.

(51) Int. Cl.
*A61B 17/80* (2006.01)
(52) U.S. Cl. .................................................. 606/289
(58) Field of Classification Search .............. 606/70, 606/71, 60, 246–331
See application file for complete search history.

(56) References Cited

U.S. PATENT DOCUMENTS

| | | | | |
|---|---|---|---|---|
| 5,951,558 A * | 9/1999 | Fiz | ................................. | 606/70 |
| 6,503,250 B2 * | 1/2003 | Paul | ............................. | 606/279 |
| 6,890,335 B2 * | 5/2005 | Grabowski et al. | ............. | 606/71 |
| 6,945,973 B2 * | 9/2005 | Bray | ............................. | 606/287 |
| 7,001,387 B2 * | 2/2006 | Farris et al. | ................... | 606/287 |
| 7,004,944 B2 * | 2/2006 | Gause | .......................... | 606/294 |
| 7,060,067 B2 * | 6/2006 | Needham et al. | .......... | 606/86 B |
| 7,306,605 B2 * | 12/2007 | Ross | ............................... | 606/70 |
| 7,981,142 B2 * | 7/2011 | Konieczynski et al. | ...... | 606/290 |
| 8,016,864 B2 * | 9/2011 | Assaker et al. | ............... | 606/296 |
| 2005/0027293 A1 * | 2/2005 | LeHuec et al. | .................. | 606/61 |
| 2005/0283152 A1 * | 12/2005 | Lindemann et al. | ........... | 606/61 |
| 2007/0213728 A1 * | 9/2007 | Lindemann et al. | ............ | 606/69 |

* cited by examiner

*Primary Examiner* — Kevin T Truong
*Assistant Examiner* — Christopher Beccia
(74) *Attorney, Agent, or Firm* — Cermak Nakajima LLP; Adam J. Cermak

(57) ABSTRACT

A bone plating system includes a bone screw lock that includes a circular disc with a hole which is offset from the geometric center of the disc, and a tang which extends down from the disc into a circular slot on the bone plate.

5 Claims, 4 Drawing Sheets

US 8,257,408 B2

BONE PLATE AND BONE SCREW LOCKING SYSTEM

This application claims priority under 35 U.S.C. §119 to U.S. Provisional application No. 61/121,321, filed 10 Dec. 2008, the entirety of which is incorporated by reference herein.

BACKGROUND

1. Field of Endeavor

The present invention relates to devices, systems, and processes useful as bone plates, and more specifically to bone plates that are secured to one or more bones of a patient using bone screws.

2. Brief Description of the Related Art

Bone plates, including anterior cervical plates, have been used with some success over the years to bridge two or more bones, or portions of bones. Examples are described in the numerous patents to Michelson, including U.S. Pat. No. 6,193,721 ("'721 patent"), and all of its progeny, the entireties of which are incorporated by reference herein.

As described in the '721 patent, it is oftentimes useful to provide the bone plate with a locking system for the bone screws, to inhibit the bone screws from backing out. While the '721 patent describes several such bone screw lock systems, they are not without their drawbacks. For example, bone screw locks which include a notched perimeter must be very precisely manufactured so that a bone screw can be inserted past the lock and into its respective bone screw hole in the bone plate, which increases the cost of manufacturing such locks. And, the rotational position of the lock must also be carefully set by the surgeon, so that the bone screw lock does not actually inhibit insertion of the bone screw into the plate by misalignment of the lock with respect to the bone screw hole.

There remains a need in bone plates for a bone screw lock which is simple to use by the surgeon, easier and less costly to manufacture, and still inhibit the backing out of bone screws from their respective holes in bone plates.

SUMMARY

According to a first aspect of the invention, a bone plate, usable with at least two bone screws to be attached to bone, comprises a plate having a top surface and a bottom surface, two bone screw holes formed through the plate between the top and bottom surface, each bone screw hole having a center, the two bone screw holes defining a line between the two bone screw hole centers, a hole configured and arranged to receive a bone screw lock system, the hole extending through the plate and positioned a distance Y from said line, a semi-circular groove formed in the top surface of the plate and having two groove ends, and a bone screw lock system including a lock element having an upper surface, a lower surface, a geometric center, and a hole extending through the disc between the upper and lower surfaces, the hole having a geometric center which is offset from the circular disc geometric center by a non-zero distance X, a tang extending from the locking element lower surface, and a retainer holding the disc to the plate at the hole, with the tang positioned in the semi-circular groove.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to exemplary embodiments of the apparatus and method, given only by way of example, and with reference to the accompanying drawings, in which.

DETAILED DESCRIPTION OF EXEMPLARY EMBODIMENTS

Figure 1:
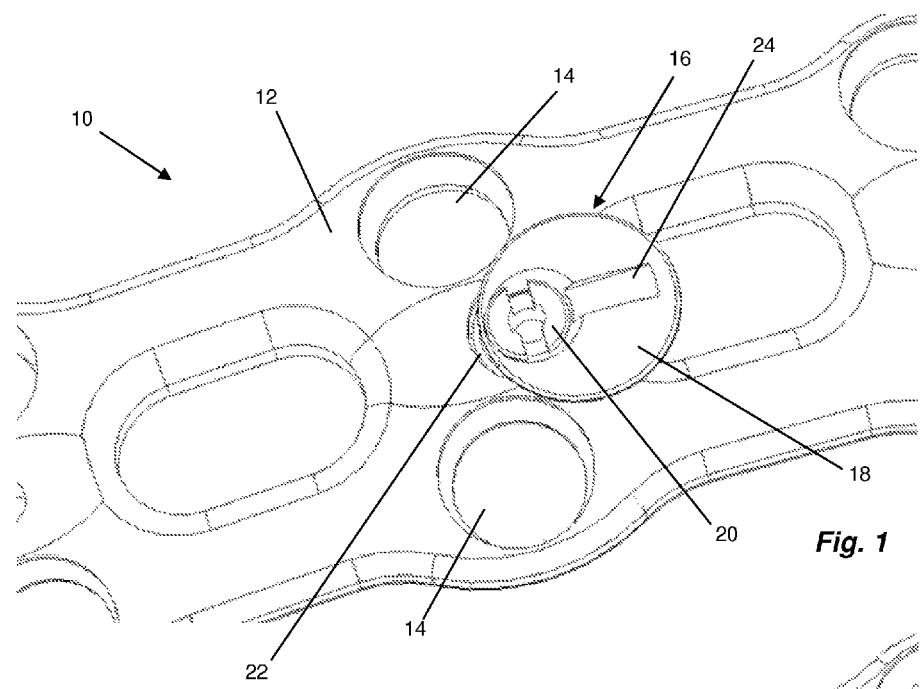
FIG. 1 illustrates a top, front, right perspective view of portions of a first exemplary embodiment of a bone screw locking system and bone plate, adhering to principles of the present invention, with the locking system in an unlocked orientation.

Referring to the drawing figures, like reference numerals designate identical or corresponding elements throughout the several figures.

List of Reference Numerals

10 bone plate system
12 plate
14 bone screw hole(s)
16 bone screw lock system
18 circular disc
20 retainer
22 C- or U-shaped track or groove
24 surface feature
26 hole through disc 18
28 center of hole 26
30 center of disc 18
32 tang
34 frustoconical portion of hole 26
36 cylindrical portion of hole 26
38 upper surface of disc 18
40 lower surface of disc 18
42 end of groove 22
44 end of groove 22
46 hole in plate 12 for retainer 20
100 bone plate system
102 bone screw lock
104 circular disc
106 surface feature
108 retainer
H height of tang 32
D distance from center 28 of hole 26 to center of tang 32

W width of tang 32 along direction of D
R distance from center of hole 46 to center of groove 22
X distance between the center of hole 26 to the center of disc 18
Y distance between the center of hole 46 to the midline of holes 14
Z width of groove 22

FIG. 1 illustrates a first exemplary embodiment of a bone plate system 10 embodying principles of the present invention, the bone screws not having been illustrated in order to simplify the drawing disclosure. The bone screw lock 16 is attached to the plate 12 by a retainer 20, which can be either a removable device (e.g., a screw), permanent device (e.g., a rivet), or a hybrid device. While the drawing figures illustrate the bone screw lock 16 including a circular disc 18, other locks embodying principles of the present invention are not restricted to the inclusion of a disc 18, and instead can include a corresponding element which is not disc-shaped, so long as the corresponding element is configured to perform the same functions as the disc 18, and in particular has a lateral dimension which corresponds to the diameter or radius of the disc 18 sufficient to perform the same function as the disc 18. By way of non-limiting example, the disc 18 can be replaced with a corresponding element having a star-shape, a T-shape, an I-shape, a V-shape, or a cross- or X-shape.

FIG. 1 illustrates the bone screw lock in an orientation in which the bone screws in the two adjacent bone screw holes are not present or not locked in place, because the disc 18 does not overlap either of the holes. Optionally, the disc 18 can have a larger or smaller diameter, so that it can be oriented to overlap only one of the holes at a time.

Figure 2:
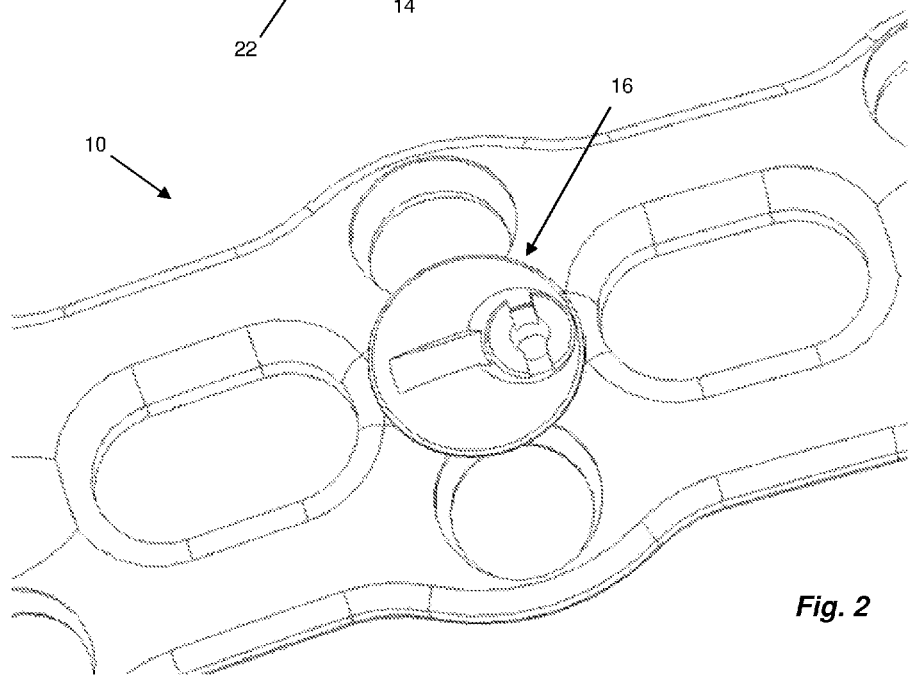
FIG. 2 illustrates a top, front, right perspective view of portions of the bone screw locking system of FIG. 1, with the locking system in a locked orientation.
Figure 3:
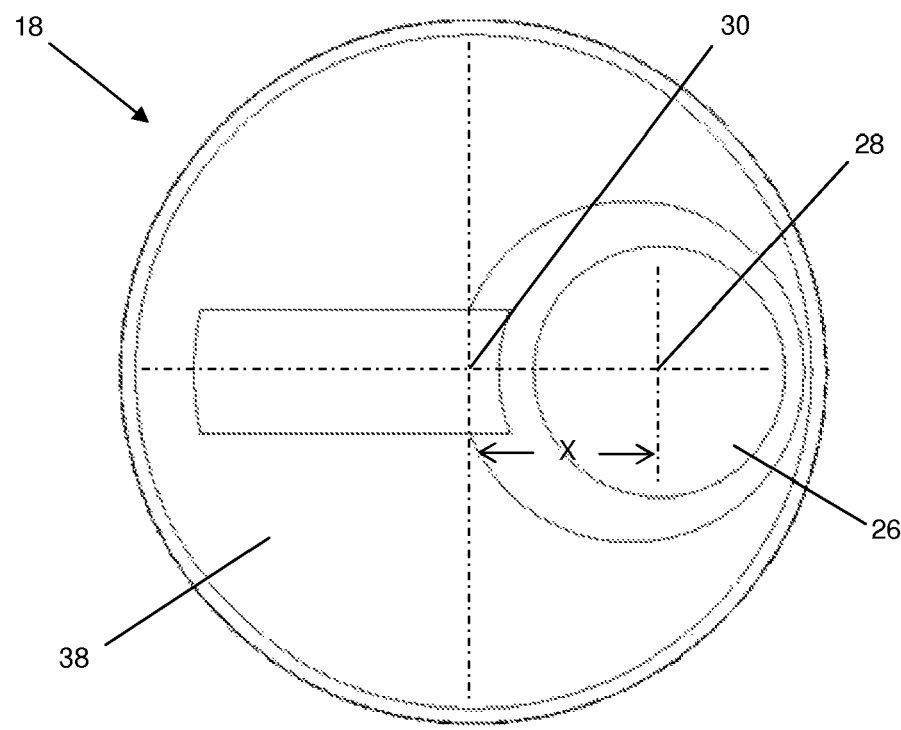
FIG. 3 illustrates a top plan view of a portion of the locking system of FIG. 1.
Figure 4:
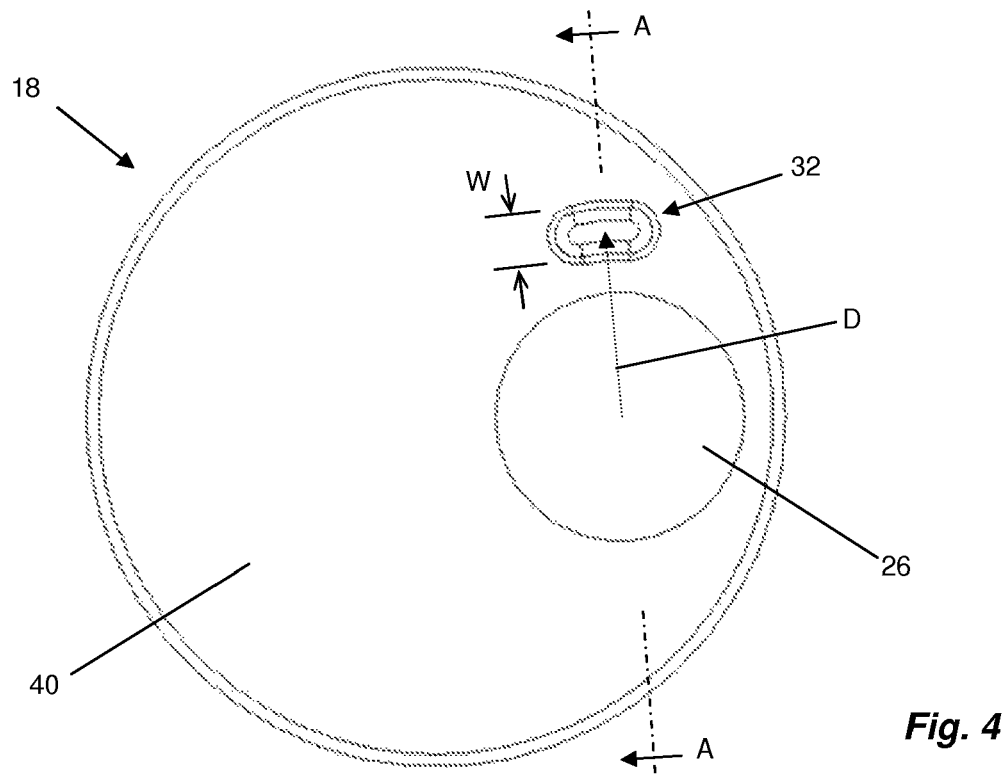
FIG. 4 illustrates a bottom plan view of a portion of the locking system of FIG. 1.
Figure 5:
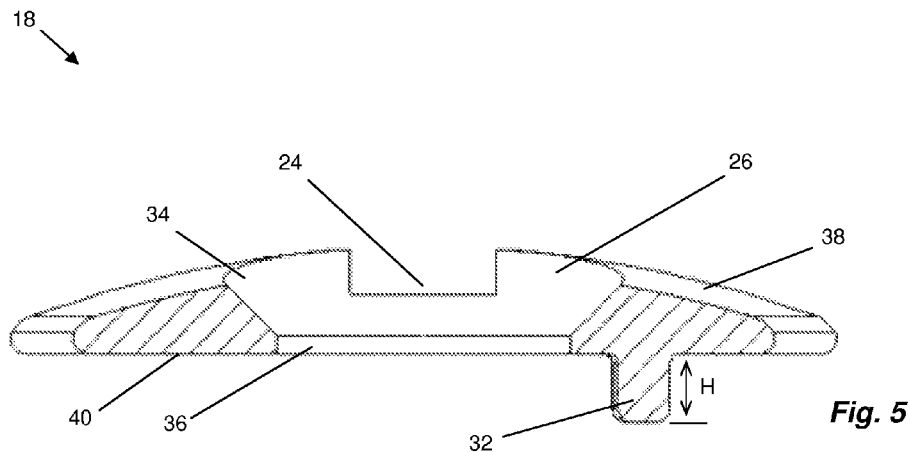
FIG. 5 illustrates a cross-sectional view taken at line A-A in FIG. 4.
Figure 6:
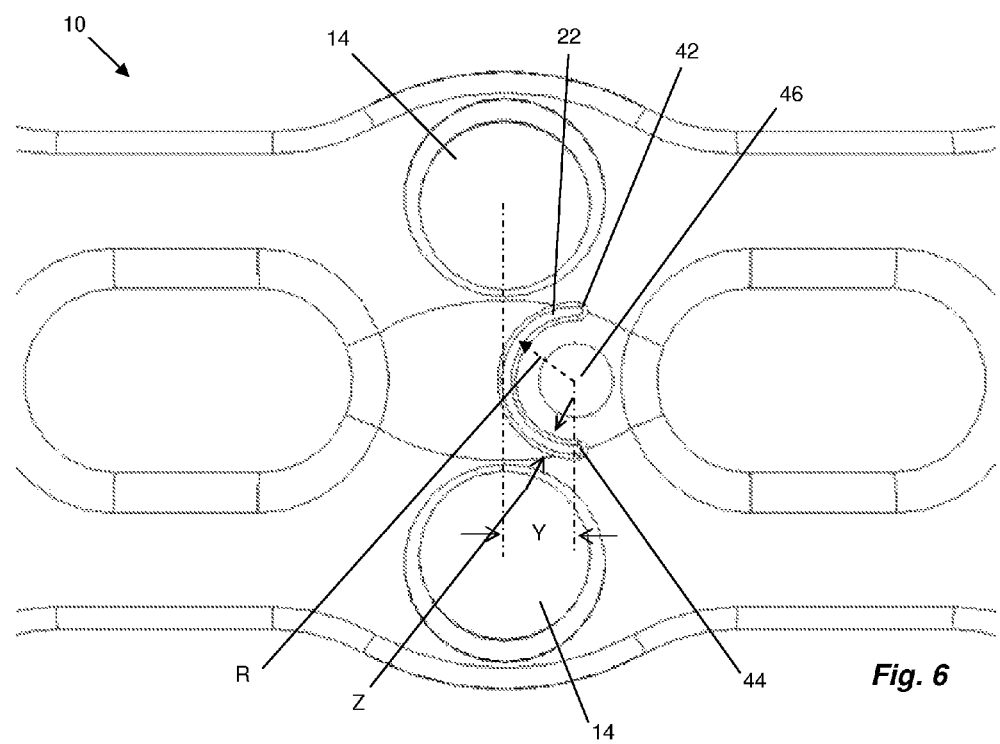
FIG. 6 illustrates a top plan view of the bone plate of FIG. 1, with portions of the bone screw locking system removed.

The hole 26 through the disc 18 is offset from the geometric center 30 of the disc, so that the disc can be rotated from the orientation illustrated in FIG. 1 to the orientation illustrated in FIG. 2, in which the disc 18 overlies both of the adjacent bone screw holes and, therefore, locks in the holes the bone screws that have been installed in those holes. In order to achieve this result, the distance X between the centers 28, 30, the distance Y between the center of hole 46 to the midline of holes 14, and the diameter of the disc 18 are together selected so that, in the first orientation (of FIG. 1), the disc 18 does not overlie either of the holes 14, and in the second orientation (of FIG. 2), the disc 18 overlies both holes 14. Alternatively, these dimensions can be selected so that, slightly different from the orientation illustrated in FIG. 1, the disc 18 overlies only one hole, while permitting free access to the other hole 14.

The surface feature 24 is provided to permit the practitioner to insert a tool to push against the disc 18 to rotate it, and can be a slot or the like, as illustrated.

Optionally, the system 16 also includes a stop or tang 32 on the bottom surface 40 of the disc (or a corresponding element, with a different shape) 18, which is received and rides in a groove or track 22 formed in the top surface of the plate 12. Because the disc 18 rotates simply in the hole 46, held there by the retainer 20, the groove 22 is a portion of a circle, and advantageously is less than a complete circular groove and includes ends 42, 44. The tang 32 has a width less than the track width, is set a distance D that is the same as the distance R of the groove 22 from the center of the hole 46, and causes the disc 18 to stop along its circular motion when the tang hits one of the groove ends 42, 44.

Figure 7:
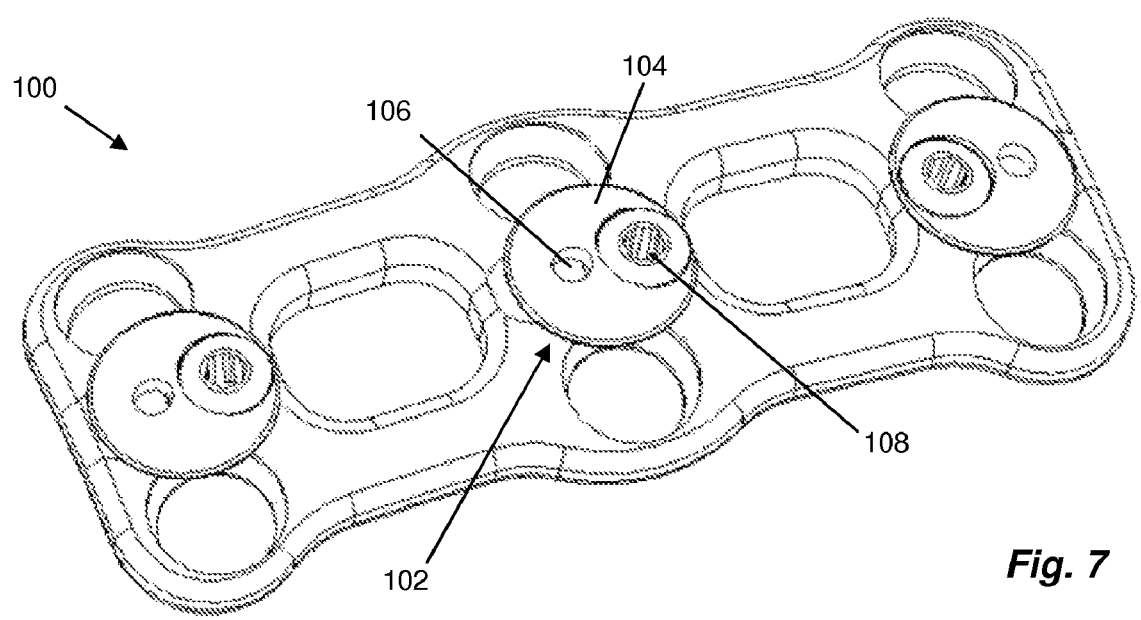
FIG. 7 illustrates a top, front, right perspective view a second exemplary embodiment of a bone screw locking system and bone plate, adhering to principles of the present invention, with the locking system in a locked orientation.

FIG. 7 illustrates a second exemplary embodiment 100, in which the surface feature is a through hole 100, the retainer 108 has a different torque transmitting profile, e.g., a hexagon to receive an Allen wrench or the like, and each set of two bone screw holes is provided with a bone screw lock system 102.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

We claim:

1. A bone plate usable with at least two bone screws to be attached to bone, the plate comprising:
   a plate having a top surface and a bottom surface;
   two bone screw holes formed through the plate between the top and bottom surface, each bone screw hole having a center, the two bone screw holes defining a line between the two bone screw hole centers;
   a plate hole configured and arranged to receive a bone screw lock system, the plate hole extending through the plate and positioned a distance Y from said line;
   a semi-circular groove formed in the top surface of the plate and having two groove ends; and
   a bone screw lock system including
      a lock element having an upper surface, a lower surface, a geometric center, and a lock hole extending through the lock element between the upper and lower surfaces, the lock hole having a geometric center which is offset from the lock element geometric center by a non-zero distance X;
      a tang extending from the lock element lower surface; and
      a retainer holding the lock element to the plate at the lock hole, with the tang positioned in the semi-circular groove.

2. A bone plate according to claim 1, wherein the groove is positioned between the two bone screw holes.

3. A bone plate according to claim 1, wherein the distance Y, the distance X, and the lateral size of the locking element are together selected so that, when the tang is positioned against a first of said groove ends, the locking element does not overlie either of said two bone screw holes, and when the tang is positioned against a second of said groove ends, the locking element overlies both of said two bone screw holes.

4. A bone plate according to claim 1, wherein the distance Y, the distance X, and the diameter of the circular disc are together selected so that, when the tang is positioned against a first of said groove ends, the locking element overlies only one of said two bone screw holes, and when the tang is positioned against a second of said groove ends, the locking element overlies both of said two bone screw holes.

5. A bone plate according to claim 1, wherein the lock element has a shape selected from the group consisting of circular, a star-shape, a T-shape, an I-shape, a V-shape, a cross-shape, and an X-shape.

* * * * *